United States Patent [19]

Lang et al.

[11] Patent Number: 4,726,942
[45] Date of Patent: Feb. 23, 1988

[54] COSMETIC COMPOSITION FOR PROTECTION AGAINST ULTRAVIOLET RADIATION AND ITS USE FOR THIS PURPOSE

[75] Inventors: Gerard Lang, Saint-Gratien; Alain Malaval, Marly-la-Ville; Madeleine Leduc, Paris, all of France

[73] Assignee: L'Oreal, Paris, France

[21] Appl. No.: 575,754

[22] Filed: Feb. 1, 1984

[30] Foreign Application Priority Data

Feb. 3, 1983 [FR] France .............................. 83 01715

[51] Int. Cl.[4] .................. A61K 7/42; A61K 7/44; A61K 9/10; A61K 9/12
[52] U.S. Cl. ............................ 424/47; 424/DIG. 5; 424/59; 424/60; 424/61; 424/63; 424/64; 424/70; 514/937; 514/944
[58] Field of Search ................ 424/70, 61, 59, 64, 424/63, 365, 60, 47

[56] References Cited

U.S. PATENT DOCUMENTS

| | | | |
|---|---|---|---|
| 3,272,855 | 9/1966 | Strobel et al. | 260/465 D |
| 3,275,520 | 9/1966 | Strobel | 260/465 D |
| 3,278,448 | 10/1966 | Laurer et al. | 260/465 D |
| 3,546,270 | 12/1970 | Kirchmayr et al. | 260/465 D |
| 3,629,193 | 12/1971 | Metzner et al. | 260/45.85 |
| 3,634,320 | 1/1972 | Metzmer et al. | 260/45.85 R |
| 3,748,131 | 7/1973 | Reynolds et al. | 96/35.1 |
| 3,781,417 | 12/1973 | Welters et al. | 424/59 |
| 3,860,598 | 1/1975 | Rosenkranz et al. | 260/287 R |
| 4,061,730 | 12/1977 | Kalopissis et al. | 424/59 |
| 4,165,336 | 8/1979 | Bouillon et al. | 260/511 |
| 4,250,108 | 2/1981 | Bouillon et al. | 260/511 |
| 4,290,974 | 9/1981 | Bouillon et al. | 260/511 |
| 4,304,730 | 12/1981 | Bouillon et al. | 260/429.9 |
| 4,323,549 | 4/1982 | Bouillon et al. | 424/45 |
| 4,327,031 | 4/1982 | Bouillon et al. | 260/429.9 |
| 4,330,488 | 5/1982 | Bouillon et al. | 260/511 |
| 4,406,880 | 9/1983 | Bouillon et al. | 424/40 |
| 4,421,739 | 12/1983 | Bouillon et al. | 424/47 |

FOREIGN PATENT DOCUMENTS

| | | | |
|---|---|---|---|
| 1492323 | 1/1969 | Fed. Rep. of Germany | 424/69 |
| 0056410 | 4/1982 | Japan | 424/61 |
| 0080311 | 5/1982 | Japan | 424/61 |
| 1064116 | 4/1967 | United Kingdom | 424/60 |

OTHER PUBLICATIONS

Suzuki et al, "Four-Center Type Photopolymerization in the Solid State, III, Polymerization of Phenylene Diacrylic Acid and its Derivatives", 1969, pp. 2319-2331.

Nakanishi et al, "Four-Center Type Photopolymerization in the Solid State, IV, Polymerization of alpha-alpha'-Dicyano-p-benzenediacrylic Acid and Its Derivatives*", 1970, pp. 2151-2160.

Willis et al, "Effects of Long Ultraviolet Rays on Human Skin: Photo-Protective or Photoaugmentative?", *The Journal of Investigative Dermatology*, vol. 59, No. 6, 1972, pp. 416-420.

Primary Examiner—Dale R. Ore
Attorney, Agent, or Firm—Fleit, Jacobson, Cohn & Price

[57] ABSTRACT

A cosmetic composition for protection against ultraviolet radiation and its use for this purpose.

The present invention relates to a cosmetic composition containing, as an agent for protecting against the UV rays at least one compound of the formula

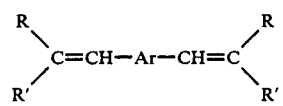

where Ar denotes an m- or p-phenylene or biphenylene radical capable of being substituted by one or more halogen atoms, one or more $C_1$–$C_6$ lower alkyl or lower alkoxy groups, R denotes a hydrogen atom, an ester group —$COOR_1$, an amide group —$CONR_1R_2$ or a nitrile group;

R' denotes an ester group —$COOR_1$ or amide group —$CONR_1R_2$; in addition when R denotes a hydrogen atom, R' can be an acid group —COOH or its salts, $R_1$ being capable of being a linear, branched or cyclic, saturated or unsaturated carbon chain containing up to 18 carbon atoms, unsubstituted or substituted by one or more hydroxyl, alkoxy, amino or quaternary ammonium groups, $R_2$ being capable of being a hydrogen atom or a $C_1$–$C_6$ lower alkyl group, in a cosmetically acceptable medium.

16 Claims, No Drawings

COSMETIC COMPOSITION FOR PROTECTION AGAINST ULTRAVIOLET RADIATION AND ITS USE FOR THIS PURPOSE

The present invention relates to a cosmetic composition employed as an agent for protecting, particularly human skin, against UV rays.

It is known that light rays of wavelengths between 280 and 400 nm permit the browning of human skin and that rays of wavelengths between 280 and 320 nm known under the term UV-B also cause erythemas and cutaneous burns which can be harmful to the development of a suntan.

The use of numerous compounds active in the above-mentioned wavelengths range of 280-320 nm is already known.

It is also known that UV-A rays of wavelengths between 320 and 400 nm cause browning of the skin but can also cause a change in the latter, particularly in the case of a sensitive skin or a skin continually exposed to solar radiation. It has been found that UV-A rays can augment the action of the UV-B rays as has been described by several groups of authors and more particularly by J. WILLIS, A. KLIGMAN and J. EPSTEIN (The Journal of Investigative Dermatology, Vol. 59, no. 6, page 416, 1973) under the name of Photo augmentation. The UV-A rays promote the triggering of the erythemic reaction or augment this reaction in some individuals. Similarly, they can be the cause of photo-toxic or photo-allergic reactions.

It has therefore appeared desirable to filter the UV-A rays as well. Compounds capable of filtering UV-A rays, particularly dibenzoylmethane derivatives, are known but the number of these compounds remains relatively limited.

Furthermore, it has appeared advantageous to investigate compounds absorbing UV rays over a wide range, to filter both the UV-A and the UV-B rays. This is the case, for example, of the 3-para-oxybenzylidene-2-bornanones of French Patent Application No. 2,430,938 or of 3-cinnamylidene camphor of U.S. Pat. No. 3,781,417.

It is also known that the components present in the cosmetic preparations and in particular some colourants of dyeing compositions, coloured hair lacquers, shampoos, hair-setting lotions, makeup products such as tinted creams, nail varnishes and lipsticks, do not always have sufficient light stability and deteriorate under the effect of light radiations.

We have therefore investigated compounds capable of absorbing both the UV-A rays and the UV-B rays over the widest possible range of wavelengths and capable of providing protection both to human skin and to various products sensitive to UV radiations, these compounds having to possess, in addition to good absorption qualities, a good thermal and photochemical stability, as well as a wide range of solubilities in the media usually employed in cosmetics.

Thus we have found that compounds of the formula (I) below had good filtering properties in a wide range of wavelengths extending from 270 to 400 nm and particularly from 305 to 360 nm, whilst possessing an excellent thermal and photochemical stability and having the advantage of being neither toxic nor irritant and being perfectly harmless to the skin.

The compounds employed according to the present invention have the formula:

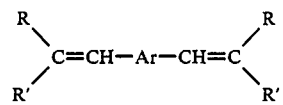

in which
Ar denotes a m- or p-phenylene or biphenylene radical capable of being substituted by one or more halogen atoms, or one or more $C_1$-$C_6$ lower alkyl or lower alkoxy groups, R denotes a hydrogen atom, an ester group —$COOR_1$, an amide group —$CONR_1R_2$ or a nitrile group, R' denotes an ester group —$COOR_1$ or amide group —$CONR_1R_2$; in addition, when R denotes a hydrogen atom, R' can be an acid group —COOH or its salts, $R_1$ being capable of being a linear, branched or cyclic, saturated or unsaturated carbon chain, substituted if appropriate by one or more hydroxyl, alkoxy, amino or quaternary ammonium groups and capable of containing up to 18 carbon atoms, $R_2$ being capable of being a hydrogen atom or a $C_1$-$C_6$ lower alkyl group.

A subject of the present invention is therefore a cosmetic composition containing as an agent for protecting against the UV rays at least one compound of the formula (I) above in a cosmetically acceptable medium.

Another subject of the present invention is a process for protecting human skin against solar radiation, and particularly the UV-A and/or UV-B rays.

In the formula (I) above, the halogen atoms may be chlorine or bromine atoms, and are preferably chlorine atoms. The lower alkyl group is preferably a $C_1$-$C_4$ alkyl group and in particular a methyl, ethyl, propyl, isopropyl, butyl, isobutyl or tertiary butyl group. The lower alkoxy group is preferably a $C_1$-$C_4$ group and more particularly denotes a methoxy, ethoxy, propoxy or butoxy group.

The radical $R_1$ preferably designates a $C_1$-$C_{10}$ radial such as for example an n-butyl, menthyl, n-octyl, 2-ethylhexyl, 2-hydroxyethyl, 2-ethoxyethyl, 2,3-dihydroxypropyl, 2-aminoethyl, 2-dimethylaminoethyl, 2-diethylaminoethyl, 3-dimethylaminopropyl, or 3-diethylaminopropyl radical and the corresponding quaternary ammonium salts.

Compounds of the formula (I) employed more particularly in the cosmetic composition of the invention are the compounds No. 1 to 16 in the following table. This table gives the wavelengths corresponding to the absorption maximum of these compounds ($\lambda_{max}$) as well as their molar extinction coefficient ($\epsilon$) and their analysis.

| Compound No. | Ar | R | R' | $R_1$ | $R_2$ | UV absorption (nm) | Analysis |
|---|---|---|---|---|---|---|---|
| | | | | | | | TBA CH$^\ominus$ assay |

-continued

| Compound No. | Ar | R | R' | $R_1$ | $R_2$ | UV absorption (nm) | Analysis | |
|---|---|---|---|---|---|---|---|---|
| 1 | phenylene | H | $CO_2H$ | — | — | $\lambda_{max}^{DMSO}$ = 320 nm ($\epsilon$ = 41,300) | Theory: 9.16 meq/g | Found: 9.35 meq/g |
| 2 | biphenylene | H | $CO_2H$ | — | — | $\lambda_{max}^{DMSO}$ = 330 nm ($\epsilon$ = 44,000) | Theory: 6.78 meq/g | Found: 6.79 meq/g |
| | | | | | | | Theory | Found |
| 3 | phenylene | $CO_2R_1$ | $CO_2R_1$ | n-butyl | — | $\lambda_{max}^{CHCl_3}$ = 323 nm ($\epsilon$ = 37,000) | % C: 67.90 % H: 7.98 | % C: 67.85 % H: 8.09 |
| 4 | 2,5-dimethoxyphenylene | $CO_2R_1$ | $CO_2R_1$ | n-butyl | — | $\lambda_{max}^{CHCl_3}$ = 395 nm ($\epsilon$ = 11,600), 305 nm ($\epsilon$ = 20,100) | % C: 65.05 % H: 7.85 | % C: 64.99 % H: 7.89 |
| 5 | phenylene | $CO_2R_1$ | $CO_2R_1$ | 2-ethylhexyl | — | $\lambda_{max}^{CHCl_3}$ = 318 nm ($\epsilon$ = 34,200) | % C: 73.17 % H: 9.88 | % C: 73.11 % H: 9.93 |
| 6 | phenylene | H | $CO_2R_1$ | 2-ethylhexyl | — | $\lambda_{max}^{CHCl_3}$ = 325 nm ($\epsilon$ = 42,700) | % C: 75.98 % H: 9.56 | % C: 75.94 % H: 9.65 |
| 7 | phenylene | CH | $CO_2R_1$ | ethyl | — | $\lambda_{max}^{CHCl_3}$ = 345 nm ($\epsilon$ = 43,800) | % C: 66.67 % H: 4.93 % N: 8.56 | % C: 66.65 % H: 4.97 % N: 8.66 |
| 8 | phenylene | CH | $CO_2R_1$ | 2-ethylhexyl | — | $\lambda_{max}^{CHCl_3}$ = 348 nm ($\epsilon$ = 45,000) | % C: 73.14 % H: 8.18 % N: 5.69 | % C: 73.24 % H: 8.12 % N: 5.62 |
| 9 | phenylene | CH | $CO_2R_1$ | menthyl | — | $\lambda_{max}^{CHCl_3}$ = 340 nm ($\epsilon$ = 48,000) | % C: 74.97 % H: 8.14 % N: 5.14 | % C: 74.91 % H: 8.16 % N: 5.11 |
| 10 | phenylene | $CONR_1R_2$ | $CONR_1R_2$ | 2-ethylhexyl | H | $\lambda_{max}^{EtOH\,(nm)}$ = 318 nm ($\epsilon$ = 31,500) | % C: 73.55 % H: 10.47 % N: 7.46 | % C: 73.69 % H: 10.50 % N: 7.27 |
| 11 | 2,5-dimethoxyphenylene | $CONR_1R_2$ | $CONR_1R_2$ | 2-ethylhexyl | H | $\lambda_{max}^{EtOH}$ = 305 nm ($\epsilon$ = 16,000) $\lambda_{max}^{EtOH}$ 380 nm ($\epsilon$ = 14,300) | % C: 71.07 % H: 10.19 % N: 6.91 | % C: 70.32 % H: 10.23 % N: 6.57 |
| 12 | phenylene | $CONR_1R_2$ | $CONR_1R_2$ | 2-ethylhexyl | H | $\lambda_{max}^{EtOH}$ = 278 nm ($\epsilon$ = 14,200) | % C: 73.55 % H: 10.47 % N: 7.46 | % C: 73.37 % H: 10.56 % N: 7.52 |

-continued

| Compound No. | Ar | R | R' | $R_1$ | $R_2$ | UV absorption (nm) | Analysis | |
|---|---|---|---|---|---|---|---|---|
| 13 | 2,3,5,6-tetramethylphenyl (H₃C, CH₃, H₃C, CH₃ substituted benzene) | CH | CONHR₁R₂ | n-octyl | H | $\lambda_{max}^{CHCl_3}$ = 315 nm ($\epsilon$ = 13,300) | % C: 74.68<br>% H: 9.22<br>% N: 10.25 | % C: 74.55<br>% H: 9.23<br>% N: 10.15 |
| 14 | biphenyl | CONR₁R₂ | CONR₁R₂ | 2-ethyl-hexyl | H | $\lambda_{max}^{EtOH}$ = 328 nm ($\epsilon$ = 42,000) | % C: 75.50<br>% H: 9.99<br>% N: 6.77 | % C: 75.29<br>% H: 10.06<br>% N: 9.66 |
| 15 | phenyl | CONR₁R₂ | CH | n-octyl | H | $\lambda_{max}^{CHCl_3}$ = 296 nm $\epsilon$ = 39070 | % C: 73.43<br>% H: 8.63<br>% N: 11.42 | % C: 73.42<br>% H: 8.67<br>% N: 11.21 |
| 16 | phenyl | H | CONR₁R₂ | n-butyl | n-butyl | $\lambda_{max}^{EtOH}$ = 322 nm $\epsilon$ = 38400 | % C: 71.95<br>% H: 10.06<br>% N: 5.99 | % C: 71.94<br>% H: 10.08<br>% N: 5,86 |

The compounds of the formula (I) employed according to the invention are liposoluble except for the acids which, when neutralised, may be soluble in water.

The acids employed according to the invention such as those of Examples 1 and 2 are obtained by condensing the corresponding dialdehydes, for example terephthalaldehyde or 4,4′-diformyldiphenyl, with malonic acid in pyridine in the presence of piperidine.

The diesters such as the compound of Example 6 are obtained by esterifying the above acids with an alcohol in the presence of sulphuric acid.

The tetraesters such as the compounds of Examples 3 to 5 are also prepared in a known manner by condensing the corresponding dialdehyde, for example 2,5-dimethoxyterephthalaldehyde or terephthalaldehyde, with a malonate such as n-butyl malonate or 2-ethylhexyl malonate. The dialdehydes are commercial products or are prepared by conventional methods, for example by chloromethylation followed by the Sommelet reaction. The malonates are synthesized from malonic acid and the corresponding alcohols in benzene or toluene in the presence of sulphuric acid by eliminating the water formed in the course of the esterification.

The cyanoesters according to the invention such as those of Examples 7 to 9 are prepared by the condensation of the corresponding dialdehydes with cyanoacetates in ethanol in the presence of potassium fluoride. The cyanoacetates are themselves prepared by the esterification of cyanoacetic acid with the corresponding alcohols in toluene in the presence of sulphuric acid, or are commercial products.

The diamides according to the invention such as the compound of Example 16, are obtained by reacting the chloride of the corresponding diacid with an amine in methylene chloride.

The tetra-amides according to the invention, such as the compounds of Examples 10 to 12 and 14, are obtained by the condensation of a malonamide, for example N-2-ethylhexyl malonamide with an aromatic dialdehyde, for example terephthalaldehyde, isophthalaldehyde, 2,5-dimethoxyterephthalaldehyde or 4,4′-diformyldiphenyl, in the presence of piperidine acetate in toluene under reflux over a period of about twenty hours.

The cyanoamides according to the invention, such as the compounds of Examples 13 and 15, are obtained by the condensation of a cyanoacetamide, such as N-octyl cyanoacetamide, with an aromatic dialdehyde such as tetramethyl terephthalaldehyde or isophthalaldehyde in ethanol, in the presence of potassium fluoride.

According to a first embodiment of the present invention the cosmetic composition forming the subject of the present application is a composition intended to protect human skin against ultraviolet rays. It can therefore be presented in the most diversified forms usually employed for this type of composition. It is presented in particular in the form of a solution, lotion, gel, an emulsion such as a cream or a milk, a solid stick or may be packaged as an aerosol.

It may also contain cosmetic adjuvants usually employed in this type of composition such as thickeners, softeners, humectants, super-fatting agents, emollients, wetting agents, surfactants, preservatives, anti-foams, perfumes, oils, waxes, colourants and/or pigments intended to colour the composition itself or the skin, or any other ingredient usually employed in cosmetics.

The compound of the formula (I) is present particularly in proportions by weight of between 0.1 and 15% relative to the total weight of the composition.

A monoalcohol or a lower polyol or their mixtures or an aqueous alcohol solution may be employed as a solubilising solvent. The monoalcohols or polyols which are particularly preferred are ethanol, isopropanol, propylene glycol or glycerol.

An embodiment of the invention is an emulsion in the form of a protective cream or milk comprising, in addition to the compound of the formula (I), fatty alcohols, ethoxylated or glycerolated fatty alcohols, fatty acid esters and particularly fatty acid triglycerides, fatty acids, lanolin, natural or synthetic oils, or waxes, in the presence of water.

Another embodiment consists of lotions such as oil-alcohol lotions based on a lower alcohol such as ethanol, or a glycol such as propylene glycol and/or a polyol such as glycerol and fatty acid esters such as fatty acid triglycerides.

The cosmetic composition of the invention can also be an aqueous-alcoholic gel comprising one or more lower alcohols such as ethanol, propylene glycol or glycerol, and a thickener, in the presence of water.

The present invention also applies to cosmetic sunscreen compositions containing at least one compound of the formula (I) which may be associated with other sunlight filters specific for the UV-B radiation and/or the UV-A radiation and compatible with the compounds according to the invention. It is therefore possible to obtain a formulation filtering all of the UV-B and UV-A radiations.

The compounds according to the invention may be associated with UV-B filters formed by the liposoluble compounds or by oils having filtering properties such as in particular coffee oil. By way of lipophilic UV-B sunlight filters there may be mentioned salicylic acid derivatives such as 2-ethylhexyl salicylate, homomenthyl salicylate, derivatives of cinnamic acid such as 2-ethylhexyl p-methoxycinnamate, 2-ethoxyethyl p-methoxycinnamate, derivatives of p-aminobenzoic acid such as amyl p-aminobenzoate, 2-ethylhexyl p-dimethylaminobenzoate, benzophenone derivatives such as 2-hydroxy-4-methoxybenzophenone, camphor derivatives such as 3-(4'-methylbenzylidene) camphor, if appropriate in combination with 4-isopropyldibenzoyl methane or 3-benzylidene camphor.

By way of water-soluble sunlight filters filtering the UV-B rays which may also be associated with the liposoluble or water-soluble filters of the invention, provided they are compatible with the latter, there may be mentioned the benzylidene camphor derivatives described in French Pat. Nos. 2,199,971, 2,236,515 and 2,383,904 and more particularly 4-(2-oxo-3-bornylidenemethyl)-phenyltrimethylammonium methylsulphate, and the salts of 4-(2-oxo-3-bornylidenemethyl)-benzenesulphonic acid, 2-methyl-5-(2-oxo-3-bornylidenemethyl)benzenesulphonic acid and 2-phenyl-benzimidazole-5-sulphonic acid.

The compounds according to the invention may also be associated with UV-A filters among which there may be mentioned dibenzoylmethane derivatives.

It is to be understood that the list of sunlight filters employed in combination with the compounds (I) according to the invention which is given above is not exhaustive.

The sunscreen compositions according to the invention may be presented in the form of solutions, lotions, emulsions such as a cream or a milk, in the form of oils, oily gels, aqueous-alcoholic or alcoholic gels, or may be packaged as aerosols or solid sticks. They may incorporate the abovementioned cosmetic adjuvants usually employed in compositions of this type.

The present invention also applies to cosmetic compositions, coloured or uncoloured, containing at least one compound of the formula (I) as an agent for protection against ultraviolet rays.

These compositions may consist of hair-care compositions such as hair lacquers, hairsetting and, if appropriate, conditioning or untangling lotions, shampoos, colouring shampoos, hair dyeing compositions, makeup products such as nail varnishes, skin conditioning creams, foundations, or lipsticks, as well as any other cosmetic composition which, on account of its constituents, may present problems of stability to light during storage.

The invention also applies to a process for protecting human skin against UV-A rays and/or UV-B rays consisting in applying to the skin an effective quantity of a cosmetic composition containing at least one compound of the formula (I), associated if appropriate with other agents absorbing the UV-A and/or UV-B rays in a cosmetically acceptable medium.

The invention is illustrated by the non-limiting examples of use below.

EXAMPLE 1

Protective day cream

| | |
|---|---|
| Compound No. 4: 2,5-dimethoxy-1,4-phenylene-bis(butyl α-carboxybutyl acrylate) | 1 g |
| Polyoxyethyleneated fatty alcohols | 7 g |
| Fatty acid triglycerides | 30 g |
| Glycerol monostearate | 2 g |
| Silicone oil | 1.5 g |
| Cetyl alcohol | 1.5 g |
| Preservatives | 0.3 g |
| Perfume | 0.6 g |
| Demineralised water q.s. | 100 g |

To prepare this cream the fatty materials are heated to 80°–85° C.; the filter of formula (I) is added. Moreover, water is heated to 80°–85° C. and the fatty phase is added with vigorous stirring to the aqueous phase; stirring is continued for 10 to 15 minutes, then the mixture is allowed to cool with moderate stirring and the perfume is added at approximately 40° C.

EXAMPLE 2

Protective day cream

| | |
|---|---|
| Compound No. 7: p-phenylenebis(ethyl α-cyanoacrylate) | 0.5 g |
| Benzylidene camphor | 0.5 g |
| Triglycerides of fatty acids ($C_8$ to $C_{12}$) | 31 g |
| Glycerol monostearate | 6 g |
| Stearic acid | 2 g |
| Cetyl alcohol | 1.2 g |
| Lanolin | 4 g |
| Preservatives | 0.3 g |
| Propanediol | 2 g |
| Triethanolamine | 0.5 g |
| Perfume | 0.5 g |
| Demineralised water q.s. | 100 g |

The fatty materials are heated to 80°–85° C. and the filters are added; the fatty phase is added with vigorous stirring to water (containing the water-soluble compounds) previously heated to 80°–85° C. After 15 minutes vigorous stirring, the mixture is allowed to cool with moderate stirring.

EXAMPLE 3

Protective milk

| | |
|---|---|
| Compound No. 3: p-phenylenebis(butyl α-carboxybutyl acrylate) | 0.5 g |
| Octyl p-dimethylaminobenzoate | 0.5 g |
| Cetyl stearyl alcohol | 2 g |
| Cetyl alcohol | 2 g |
| Triglycerides of fatty acids ($C_8$ to $C_{12}$) | 20 g |

| -continued | |
|---|---|
| Lanolin | 4 g |
| Stearic acid | 0.5 g |
| Preservatives | 0.3 g |
| Carbopol 934 (crosslinked polyacrylic acid sold by the GOODRICH CHEMICAL Company) | 0.15 g |
| Triethanolamine | 0.2 g |
| Perfume | 0.4 g |
| Demineralised water q.s. | 100 g |

The emulsion is prepared in the same manner as in Example 1.

EXAMPLE 4

Oil-alcohol sunscreen lotion

| | |
|---|---|
| Compound No. 5: phenylenebis(2-ethylhexyl α-carboxy-2-ethylhexylacrylate) | 3.5 g |
| 2-Ethylhexyl p-methoxycinnamate | 2 g |
| Perfume | 0.5 g |
| 96° ethanol | 47.5 g |
| Triglycerides of fatty acids ($C_8$ to $C_{12}$)q.s. | 100 g |

The mixture of the various components is heated to 40°–45° C. to homogenise and produce a clear lotion.

EXAMPLE 5

Sunscreen cream

| | |
|---|---|
| Compound No. 6: p-phenylenebis(2-ethylhexyl acrylate) | 3 g |
| 4-[(2-Oxo-3-bornylidene)-methyl]-phenyl trimethylammonium methyl sulphate | 2.5 g |
| Polyoxyethyleneated fatty alcohols | 7 g |
| Triglycerides of fatty acids ($C_8$–$C_{12}$) | 30 g |
| Glycerol monostearate | 2 g |
| Silicone oil | 1.5 g |
| Cetyl alcohol | 1.5 g |
| Preservatives | 0.3 g |
| Perfume | 0.6 g |
| Demineralised water q.s. | 100 g |

The preparation of this cream is similar to that of Example 1; in this case the 4[(2-oxo-3-bornylidene)methyl]-phenyl trimethylammonium methyl sulphate is dissolved in water.

EXAMPLE 6

Sunscreen cream

| | |
|---|---|
| Compound No. 4: 2,5-dimethoxy-1,4-phenylenebis-(butyl α-carboxybutylacrylate) | 2.5 g |
| Benzylidene camphor | 4 g |
| Triglycerides of fatty acids ($C_8$ to $C_{12}$) | 31 g |
| Glycerol monostearate | 6 g |
| Stearic acid | 2 g |
| Cetyl alcohol | 1.2 g |
| Lanolin | 4 g |
| Preservatives | 0.3 g |
| Propanediol | 2 g |
| Triethanolamine | 0.5 g |
| Perfume | 0.4 g |
| Demineralised water q.s. | 100 g |

The filters are dissolved in the fatty phase. The compound No. 4 may be replaced with 2.5 g of compound No. 3.

EXAMPLE 7

Sunscreen oil

The following ingredients are mixed, and, if necessary, heated to 40°–45° C. for homogenising:

| | |
|---|---|
| Compound No. 5: p-phenylenebis(2-ethylhexyl α-carboxy-2-ethylhexylacrylate) | 3 g |
| Octyl p-dimethylaminobenzoate | 3 g |
| Cocoa butter | 2.5 g |
| Antioxidants | 0.05 g |
| Perfume | 0.5 g |
| Triglycerides of fatty acids ($C_8$ to $C_{12}$)q.s. | 100 g |

EXAMPLE 8

Sunscreen gel

| | |
|---|---|
| Compound No. 12: m-phenylenebis(α-carbamyl-2-ethylhexyl N—2-ethylhexylacrylamide) | 2 g |
| 2-Ethylhexyl p-methoxycinnamate | 2.5 g |
| Cocoa butter | 5 g |
| Antioxidants | 0.05 g |
| Silica | 10 g |
| Perfume | 0.5 g |
| Triglycerides q.s. | 100 g |

This fatty gel is prepared by heating the fatty materials to 40°–45° C. and the silica is then added with vigorous stirring, followed by the filters.

EXAMPLE 9

Aqueous-alcoholic sunscreen gel

| | |
|---|---|
| Carbopol 934 | 0.7 g |
| Triethanolamine | 0.35 g |
| Propylene glycol | 25 g |
| 96° ethanol | 25 g |
| Compound No. 1: p-phenylenebis-acrylic acid in the form of triethanolamine salt | 1 g |
| Diethanolamine salt of p-methoxy-cinnamic acid | 2.5 g |
| Preservative | 0.3 g |
| Perfume | 0.4 g |
| Demineralised water q.s. | 100 g |

The Carbopol is dispersed in water with vigorous stirring, then triethanolamine is added, followed by the solvents and water in which the filters have previously been dissolved.

The same results are obtained by replacing the compound No. 1 by the compound No. 2 in the form of triethanolamine salt.

EXAMPLES 10 and 11

In these examples, the compounds of the formula (I) are employed to protect coloured compositions against the sun.

EXAMPLE 10

Coloured shampoo

| | |
|---|---|
| Triethanolamine lauryl sulphate | 10 g |
| 0.05% strength solution of Orasol BLW blue | 1 cc |
| Compound No. 2: p-biphenylenebisacrylic acid in the form of triethanolamine salt | 0.5 g |
| Perfume, preservative q.s. | |
| Water q.s. | 100 g |

EXAMPLE 11

Coloured hairsetting lotion

| | |
|---|---|
| Polyvinylpyrrolidone copolymer (of average molecular weight of 40,000, sold under the designation K30 by GAF) | 2 g |
| CR 1 solid red W 3000 (CI No. 27,290) | 0.02 g |
| Compound No. 11: 2,5-dimethoxy-1,4-phenylenebis(2-carbamyl-2-ethylhexyl N—2-ethyl-hexylacrylamide) | 0.3 g |
| 96° ethanol | 60 g |
| Water q.s. | 100 g |

EXAMPLE 12

Sunscreen stick

| | |
|---|---|
| Compound No. 13: 2,3,5,6-tetramethyl-1,4-phenylenebis(α-cyano-N—octylacrylamide) | 2 g |
| Benzylidene camphor | 2 g |
| Carnauba wax | 20 g |
| Ozokerite | 20 g |
| Lanolin | 26 g |
| Vaseline oil | 30 g |

The fatty materials are melted and the filters are dispersed therein.

EXAMPLE 13

Sunscreen stick

| | |
|---|---|
| Compound No. 10: p-phenylenebis(α-carbamyl-2-ethylhexyl N—2-ethylhexylacrylamide) | 1 g |
| p-Methylbenzylidene camphor | 1.5 g |
| Beeswax | 12.5 g |
| Ozokerite | 28 g |
| Carnauba wax | 10 g |
| Paraffin | 10 g |
| Lanolin | 12 g |
| Paraffin oil | 25 g |

EXAMPLE 14

Sunscreen oil

| | |
|---|---|
| Compound No. 15: m-phenylenebis(α-cyano-N—octylacrylamide) | 1 g |
| p-Methylbenzylidene camphor | 2 g |
| Cocoa butter | 2.5 g |
| Antioxidants, perfume q.s. | |
| Triglycerides of fatty acids, C8–C12 q.s. | 100 g |

This oil is prepared in the same manner as in Example 7.

EXAMPLE 15

Protective day cream

| | |
|---|---|
| Compound No. 16: p-phenylenebis(N,N—dibutyl-acrylamide) | 0.3 g |
| Benzylidene camphor | 0.3 g |
| Triglycerides of fatty acids, C8–C12 | 31 g |
| Glycerol monostearate | 6 g |
| Stearic acid | 2 g |
| Cetyl alcohol | 1.2 g |
| Lanolin | 4 g |
| Propanediol | 2 g |
| Triethanolamine | 0.5 g |
| Perfume, preservatives q.s. | |
| Demineralised water q.s. | 100 g |

This cream is prepared as in Example 2.

We claim:

1. A sunscreening cosmetic composition for protecting the skin against ultraviolet light radiation in the range of about 270 nm to about 400 nm, said composition comprising, an amount of between 0.1 to 15% by weight relative to the total weight of the composition of at least one compound of the formula

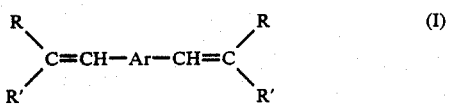

in which Ar denotes an m- or p-phenylene or biphenylene radical capable of being substituted by one or more halogen atoms, or one or more $C_1$–$C_6$ lower alkyl or lower alkoxy groups, R denotes a hydrogen atom, an ester group —$COOR_1$, an amide group —$CONR_1R_2$ or a nitrile group;

R' denotes an ester group —$COOR_1$ or amide group —$CONR_1R_2$; in addition where R denotes a hydrogen atom, R' can be an acid group —COOH or its salts, $R_1$ being capable of being a linear, branched or cyclic, saturated or unsaturated carbon chain, containing up to 18 carbon atoms, unsubstituted or substituted by one or more hydroxyl, alkoxy, amino or quaternary ammonium groups, $R_2$ being capable of being a hydrogen atom or a $C_1$–$C_6$ lower alkyl group, said composition being in a form selected from the group consisting of a lotion, a gel, an emulsion, a solid stick, and an aerosol.

2. A cosmetic composition according to claim 1, which comprises at least one compound of the formula (I) in which R denotes a hydrogen atom and R' an acid group —COOH or amide group —$CONR_1R_2$ or R denotes an amide group —$CONR_1R_2$ or nitrile group and R' an ester group $COOR_1$ or amide group —$CONR_1R_2$, or alternatively R denotes an ester group —$COOR_1$ and R' an amide group —$CONR_1R_2$, $R_1$ and $R_2$ having the same meaning as in claim 1.

3. A cosmetic composition according to claim 1, wherein the compound of the formula (I) is selected from the group consisting of p-phenylenebis(butyl α-carboxybutylacrylate), 2,5-dimethoxy-1,4-phenylenebis(butyl α-carboxybutylacrylate), p-phenylenebis(2-ethylhexyl α-carboxy-2-ethylhexyla-crylate) and p-phenylenebis(2-ethylhexyl acrylate).

4. A cosmetic composition according to claim 2, wherein the compound of the formula (I) is selected from the group consisting of p-phenylenebis-acrylic acid, p-biphenylenebis-acrylic acid, p-phenylenebis-(ethyl α-cyanoacrylate), p-phenylenebis-(2-ethylhexyl α-cyanoacrylate), p-phenylenebis-(methyl α-cyanoacrylate), p-phenylenebis-(α-carbamyl-2-ethylhexyl N-2-ethylhexylacrylamide), 2,5-dimethoxy-1,4-phenylenebis(α-carbamyl-2-ethylhexyl N-2-ethylhexylacrylamide), 2,3,5,6-tetramethyl-1,4-phenylenebis(α-cyano-N-octylacrylamide), p-biphenylene(α-carbamyl-2-ethylhexyl N-2-ethylhexylacrylamide), m-phenylenebis(α-carbamyl-2-ethylhexyl N-2-ethylhexylacrylamide), m-phenylene-bis(α-cyano-N-octylacrylamide), and p-phenylene-bis(N,N-dibutylacrylamide).

5. A cosmetic composition according to claim 1 which additionally comprises fatty alcohols, ethoxylated or glycerolated fatty alcohols, fatty acid esters, fatty acids, lanolin, natural or synthetic oils, or waxes.

6. A cosmetic composition according to claim 1 which additionally comprises a solubilising solvent such as monoalcohol or a lower polyol or their mixtures.

7. A cosmetic composition according to claim 1 which additionally comprises at least one cosmetic adjuvant selected from the group consisting of thickeners, softening agents, humectants, wetting agents, surfactants, preservatives, perfumes, oils, waxes, colourants and pigments.

8. A cosmetic sunscreen composition according to claim 1 for filtering UV-A and UV-B rays, which comprises an amount of between 0.1 to 15% by weight relative to the total weight of the composition of one compound of the formula (I) associated with other sunlight filters specific for the UV-B radiation or UV-A radiation and compatible with the compound of formula (I).

9. A cosmetic sunscreen composition according to claim 8 for filtering UV-A and UV-B rays wherein said other sunlight filter is a derivative of salicylic acid specific for UV-B radiation selected from the group consisting of 2-ethylhexyl salicylate and homomenthyl salicylate.

10. A cosmetic sunscreen composition according to claim 8 for filtering UV-A and UV-B rays wherein said other sunlight filter is a derivative of cinnamic acid specific for UV-B radiation selected from the group consisting of 2-ethylhexyl p-methoxycinnamate and 2-ethoxyethyl p-methoxycinnamate.

11. A cosmetic sunscreen composition according to claim 8 for filtering UV-A and UV-B rays wherein said other sunlight filter is a derivative of p-aminobenzoic acid specific for UV-B radiation selected from the group consisting of amyl p-aminobenzoate and 2-ethylhexyl p-dimethylaminobenzoate.

12. A cosmetic sunscreen composition according to claim 8 for filtering UV-A and UV-B rays wherein said other sunlight filter is 2-hydroxy-4-methoxybenzophenone specific for filtering UV-B radiation.

13. A cosmetic sunscreen composition according to claim 8 for filtering UV-A and UV-B rays wherein said other sunlight filter is a camphor derivative specific for UV-B radiation selected from the group consisting of 3-benzylidene camphor, 3-(4'-methylbenzylidene)camphor, 4-(2-oxo-3-bornylidene methyl)-phenyltrimethylammonium methylsulfate and the salts of 4-(2-oxo-3-bornylidene methyl)benzene sulfonic acid and 2-methyl-5-(2-oxo-3-bornylidene methyl)benzene sulfonic acid.

14. A cosmetic sunscreen composition according to claim 8 for filtering UV-A and UV-B rays wherein said other sunlight filter is coffee oil as a sunlight filter specific for the UV-B radiation.

15. A cosmetic sunscreen composition according to claim 8 for filtering UV-A and UV-B rays wherein said other sunlight filter is 4-isopropyldibenzoylmethane as a sunlight filter specific for UV-A radiation.

16. A process for protecting human skin against ultraviolet rays in the range of about 270 nm to about 400 nm which comprises applying to the skin an amount of between 0.1 to 15% by weight of at least one compound of the formula:

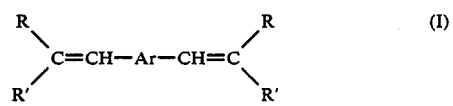

in which
Ar denotes an m- or p-phenylene or biphenylene radical capable of being substituted by one or more halogen atoms, or one or more $C_1$–$C_6$ lower alkyl or lower alkoxy groups, R denotes a hydrogen atom, an ester group —$COOR_1$, an amide group —$CONR_1R_2$ or a nitrile group;
R' denotes an ester group —$COOR_1$ or amide group —$CONR_1R_2$; in addition where R denotes a hydrogen atom, R' can be an acid group —COOH or its salts,
$R_1$ being capable of being a linear, branched or cyclic, saturated or unsaturated carbon chain, containing up to 18 carbon atoms, unsubstituted or substituted by one or more hydroxyl, alkoxy, amino or quaternary ammonium groups, $R_2$ being capable of being a hydrogen atom or a $C_1$–$C_6$ lower alkyl group, in a cosmetically acceptable medium.

* * * * *